United States Patent [19]  [11]  4,335,128
Blanchard et al.  [45]  * Jun. 15, 1982

[54] PROCESS FOR THE TREATMENT OF PATIENTS SUFFERING FROM DREPANOCYTOSIS

[75] Inventors: Jean Blanchard, Toulouse; Monique Verry, Saint-Cloud, both of France

[73] Assignee: Omnium Financier Aquitaine pour l'Hygiene et la Sante (Sanoli), Paris, France

[*] Notice: The portion of the term of this patent subsequent to Jul. 1, 1997, has been disclaimed.

[21] Appl. No.: 150,890

[22] Filed: May 19, 1980

Related U.S. Application Data

[63] Continuation of Ser. No. 917,374, Jun. 20, 1978, Pat. No. 4,210,649.

[30] Foreign Application Priority Data

Jun. 22, 1977 [FR] France ................................. 77 19161

[51] Int. Cl.$^3$ ........................................... A61K 31/435
[52] U.S. Cl. .................................................... 424/256
[58] Field of Search ......................................... 424/256

[56] References Cited
U.S. PATENT DOCUMENTS 4,051,141 9/1977 Castaigne ............................ 424/256

OTHER PUBLICATIONS

*Ann. Soc. Belge Med. Trop.*, 1969, 49, 2, 205-210, "Raper".
*The Journal of International Medical Research*, vol. 4, No. 6, 1976, pp. 375-381, "Mackenzie et al.".

Primary Examiner—Frederick E. Waddell
Attorney, Agent, or Firm—Weiser, Stapler & Spivak

[57] ABSTRACT

This invention relates to a process for the treatment of patients suffering from drepanocytosis, comprising administering to said patients a therapeutically effective dosage of a pyridine derivative having the formula:

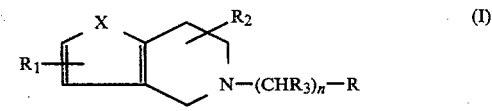

in which X is oxygen or sulfur; R is oxygen or a phenyl optionally substituted with at least a halogen, lower alkyl, lower alkoxy, nitro, amino, sulfonylamino, aryl, carboxy, alkoxycarbonyl, cyano, hydroxymethyl or methylenedioxy group; styryl, naphthyl, thienyl or benzhydryl optionally substituted with at least a halogen, lower alkyl, lower alkoxy, aryl, nitro, amino, sulfonylamino, carboxyl, alkoxycarbonyl, cyano, hydroxymethyl or methylenedioxy group; benzoyl optionally substituted with at least a halogen, lower alkyl, lower alkoxy, nitro, amino or sulfonylamino group; $R_1$ and $R_2$ each represent at least one atom or group selected from hydrogen, halogen, hydroxy, lower alkyl, lower alkoxy, nitro or amino; $R_3$ is hydrogen, halogen, hydroxy, lower alkyl, lower alkoxy, nitro or amino; and n is zero or an integer from 1 to 15; and $R_3$ may have a different meaning in each $CHR_3$ group when n is greater than 1; or a pharmaceutically acceptable acid addition salt or quaternary ammonium derivative of said compound.

10 Claims, No Drawings

PROCESS FOR THE TREATMENT OF PATIENTS SUFFERING FROM DREPANOCYTOSIS

This is a continuation, of application Ser. No. 917,374, filed June 20, 1978, now U.S. Pat. No. 4,210,649.

This invention relates to a process for the treatment of patients suffering from drepanocytosis.

Said process comprises administering to said patients a therapeutically effective dosage of a pyridine derivative having the formula:

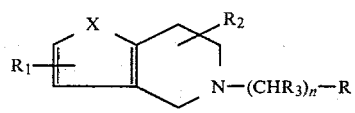

in which X is oxygen or sulfur; R is oxygen or a phenyl optionally substituted with at least a halogen, lower alkyl, lower alkoxy, nitro, amino, sulfonylamino, aryl, carboxyl, alkoxycarbonyl, cyano, hydroxymethyl or methylenedioxy group; styryl, naphthyl, thienyl or benzhydryl optionally substituted with at least a halogen, lower alkyl, lower alkoxy, aryl, nitro, amino, sulfonylamino, carboxyl, alkoxycarbonyl, cyano, hydroxymethyl or methylenedioxy group; benzoyl optionally substituted with at least a halogen, lower alkyl, lower alkoxy, nitro, amino or sulfonylamino group; $R_1$ and $R_2$ each represent at least each atom or group selected from hydrogen, halogen, hydroxy, lower alkyl, lower alkoxy, nitro or amino; $R_3$ is hydrogen, halogen, hydroxy, lower alkyl, lower alkoxy, nitro or amino; and n is zero or an integer from 1 to 15; and $R_3$ may have a different meaning in each $CHR_3$ group when n is greater than 1; or a pharmaceutically acceptable acid addition salt or quaternary ammonium derivative of said compound.

It is already known, from U.S. Pat. No. 4,051,141 and U.S. Patent Application Ser. No. 703,837, now U.S. Patent the disclosures of which are incorporated herein by reference, that these compounds have anti-inflammatory, vasodilator and blood-platelet aggregation inhibiting properties.

The compounds of the formula (I) may be prepared by methods described in the above-mentioned U.S. Patent and Application.

It has now been found that the above compounds possess also an outstanding activity for the inhibition of falciformation which make them particularly therapeutically useful for the prevention and the treatment of disorders due to drepanocytic anemia or drepanocytosis.

Drepanocytosis is a disease the origin of which is presently readily recognized by routine examinations and the elect geographical area of which is typically America, Africa and the peripheral area of the Mediterranean basin.

This disease results from a genetic defect which induces the substitution of the sixth aminoacid (Glu) of the β chain of hemoglobin with another aminoacid (Val) and which leads to the formation of S hemoglobin which is not a vehicle for oxygen. The resulting anoxia induces intravascular falciformation of the red blood corpuscles, which causes acute drepanocytic anemia with major involvements in all organs in which the blood flow is of microcirculatory type, such as the heart, the brain, the liver, the spleen, and the like.

The falciformation of the red blood corpuscles is due to the formation of rigid S hemoglobin bridges (when normally oxygenated, the hemoglobin remains dissolved in the cytoplasm of the red blood corpuscles, whereas the de-oxygenated form, i.e., S hemoglobin, develops at the level of the substituted aminoacid an adhesion site which induces the piling up of S hemoglobin molecules which precipitate as long chains and are responsible for the rigidity of the drepanocytes) in the cytoplasm of the red blood corpuscles, which prevents the latter from undergoing physiological deformation to circulate in the micro blood vessels. Since the latter have sometimes a diameter of $3\mu$ and since the red blood corpuscles have an average diameter of $7\mu$, the rigid falciform corpuscles do not circulate any longer. This stagnation is predominantly evidenced by coagulation phenomena, by the development of clots and by embolus of the microvessels.

Drepanocytosis exhibits symptoms of extreme fatigue, pain in the bones of the articulations, neurological disorders, digestive embolus, etc. From a biological standpoint, immediately after birth, in the homozygot, the hemoglobin of the foetus will gradually be substituted with S hemoglobin up to a ratio of the order of 90%, said substitution occurring within a period of time of from 1 to 15 years; in the heterozygot, the S hemoglobin will be present in an amount of 50% or higher of total hemoglobin.

Heretofore, drepanocytosis was controlled by providing the circulatory system with oxygen or by means of vincamine type drugs the vasodilator and oxygenating actions of which helped to reduce the slowing-down of the cerebral circulation. Similarly, other authors prescribed either a cocktail of antalgic drugs, or a combination of equal parts of dihydroergoconine, of dihydroergocristine and dihydroergokryptine. It should be recognized, however, that the results obtained were unsatisfactory and that only very few improvements were noted.

The therapeutic compositions containing, as active ingredient, a compound of the formula (I) act in an outstanding manner during the drepanocytosis spell, i.e., they prevent and treat the falciformation phenomenon responsible for the acute vasculoocclusive crisis of patients suffering from drepanocytosis.

Results of pharmacological and clinical tests which demonstrate the inhibiting activity of the compounds of the formula (I) on falciformation, useful in the treatment of drepanocytosis, are given below to illustrate the present addition.

Throughout the disclosure which follows, the test derivatives are referred to by the following reference numbers:

Derivative No. 1 is 5-(2-chloro-benzyl)-4,5,6,7-tetrahydrothieno[3,2-c]pyridine hydrochloride.

Derivative No. 2 is 5-(2-hydroxy-2-phenyl-ethyl)-4,5,6,7-tetrahydrothieno[3,2-c]pyridine hydrochloride.

Derivative No. 3 is 5-o.carboxybenzyl-4,5,6,7-tetrahydrothieno[3,2-c]pyridine.

Derivative No. 4 is 5-parachlorobenzyl-4,5,6,7-tetrahydrothieno[3,2-c]pyridine hydrochloride.

I. Pharmacological tests

The in vitro tests described below show that the derivatives of the formula (I) inhibit the falciformation of the red blood corpuscles and may make it reversible.

(1) Inhibition of falciformation

Blood from a patient suffering from drepanocytosis, which contains only S hemoglobin or an amount of S hemoglobin at least equal to 75% is collected over 3.8% sodium citrate sodium and is then centrifuged. The red blood corpuscles are separated from the plasma. The latter is decanted off and placed in a water-bath at 56° C. to remove the lysolecithinases, after which it is filtered. The red blood corpuscles are then diluted to 1/10 in their own plasma. The reaction is then prepared by adding to each tube of a number of tubes 2 drops of the red blood corpuscles suspension and 1 drop of solute brought to the therapeutically active dilution (about 30 $\mu$g/ml of the compound of this invention). Tubes containing 1 drop physiological saline solution are also prepared.

One drop of each solution is placed on a glass slide and covered with an object slide sealed with paraffin. The slides are left in a humid room, at the laboratory temperature.

A reading is taken at ½ hour intervals, until drepanocytes are found to appear, and the percentage is recorded for each mixture. The test is discontinued after 24 hours.

The following pharmacological data were obtained;

| Test Derivatives | Percent drepanocytes | | | | | | |
|---|---|---|---|---|---|---|---|
| | 0 hr | 1 hr | 3 hrs | 4 hrs | 6 hrs | 12 hrs | 24 hrs |
| Control | 0 | 30 | 75 | 80 | 88 | 90 | 94 |
| N° 1 | 0 | 0 | 0 | 0 | 1 | 2 | 4 |
| N° 2 | 0 | 0 | 0 | 1 | 2 | 3 | 5 |
| N° 3 | 0 | 0 | 0 | 0 | 1 | 3 | 4 |

It is apparent, from an examination of the above Table, that the effects of the compounds of the formula (I) on falciformation are obvious. Indeed, when comparing the amount of anoxic drepanocytes with that of the drepanocytes obtained under the same conditions, but after having previously added a small amount of derivative of the formula (I), it may be concluded that the inhibiting effect is quite effective because, even 24 hours later, still less than 10% drepanocytes are found to appear in these preparations.

(2) Reversibility of falciformation

The test comprises preparing a certain amount of a 5% suspension of red blood corpuscles containing S hemoglobin, in their own plasma heated at 56° C., as in the preceding test. This suspension is then added to as many hemolysis tubes as there are different test compounds.

After covering the red blood corpuscle suspension with a layer of paraffin oil, the tubes are left at laboratory temperature until falciformation is complete, which phenomenon occurs within a period of time of 6 hours.

To each tube is then added a 1/10 volume of physiological saline and of suitably diluted derivative of the formula (I). The tubes are then left at laboratory temperature for 10-15 minutes; after which 10% formaldehyde is added to each tube and the number of irreversible drepanocytes in each tube is then counted.

The results obtained show that when a small amount (1/10 by volume) of derivative of the formula (I) is added to a suspension of falciform and anoxic red blood corpuscles containing S hemoglobin, reversibility of the phenomenon occurs immediately. The appearance of the cells is characteristic: the drepanocytes lose their shape and revert to a disk-like shape. The membrane, however, remains highly visible; the red blood corpuscles become transparent; nevertheless, some erythrocytes retain the shape of crystalline S hemoglobin.

II. Clinical tests

The derivatives of the formula (I) were administered to patients suffering from drepanocytosis. Some of the case histories are reported below:

Case report No. 1

M. B., a 24 year old Senegalese student, suffers from drepanocytosis discovered in 1970. He exhibited many spells of the disease and was administered several transfusions. He underwent treatments with vincamine and the mixture of the alkaloids of ergot of rye: all treatments failed.

In 1976, M. B. exhibited pain in the ribs, after a cold bath. He exhibits extreme listlessness and fatigability; he also exhibits substantial icterus and rheumatic pains; palpation of the spleen is impossible, M.B. considers that sports, exposure to cold and cold baths, apnea and infections are responsible for the drepanocytic spells.

His drepanocytic condition is confirmed by electrophoresis which discloses the presence of S hemoglobin. X-ray examination of the bones of the lower and upper limbs and of the lumbar rachis shows, on one hand, the lightening of the bone structure at the level of the ephiphisis of the tibia and the fibula, and, on the other hand, a striated appearance of the bone structure of the rachis. Biological and blood tests confirm that M. B. suffers from a drepanocytic condition and anemia.

The patient is then treated with 750 mg/day of derivative No. 1 (3 coated tablets each containing 250 mg active ingredient). The drepanocytic spells are soon found to stop, within a few days. The patient feels markedly less tired, is less jaundiced; he may also undertake some physical efforts without undue consequences, whereas, without treatment, these release drepanocytic spells. From a biological standpoint, there is also marked improvement after two months of treatment.

| Control test | Before treatment | After treatment |
|---|---|---|
| Red Blood Corpuscles | 2,400,000 | 2,500,000 |
| White Blood Corpuscles | 8,500 | 8,000 |
| Hemoglobin | 8 g | 9,5 g |
| Hematocrite | 26% | 31% |
| Total Bilirubin | 60 | 20 |
| Reticulocytes | 10% | 10% |

Case Report No. 2

M. N'D, 16 years old, suffers, since the age of 2, from a drepanocytosis which was diagnosed by electrophoresis. The drepanocytic spells appeared when the patient was 11 years old. He was hospitalized a number of times for predominantly articular pain in the bones. In this African boy, cold and physical effort are the factors which trigger the drepanocytic spells which occur regularly 3–5 times a month, each spell lasting about 48 hours. Treatments with vincamine and the combination of the alkaloids of ergot failed consistently. Young N'D was then treated daily, for 6 weeks, with 800 mg of derivative No. 2 (4 capsules containing each 200 mg active ingredient). No drepanocytic spell was noted during the treatment; clinical improvement of the condition of the patient was also found to be satisfactory. Thus, M. N'D. is able to sustain physical efforts which, previously, induced the drepanocytic spells. There is also considerable decrease of the asthenia, together with some recovery of the patient's activity.

This therapeutic improvement is confirmed biologically:

| Control tests | Before treatment | After treatment |
| --- | --- | --- |
| Red blood corpuscules | 2,700,000 | 3,200,000 |
| White blood corpuscules | 8,500 | 8,000 |
| Hemoglobin | 8 g | 9.5 g |
| Hematocrite | 26% | 31% |
| Total Bilirubin | 60 | 20 |
| Reticulocytes | 10% | 10% |

Case report No. 3

M. R. D. is a 37 year old African male nurse. He suffers from drepanocytic anemia which was detected by electrophoresis. He is asthenic and has extreme listlessness. The factors which trigger his drepanocytic spells are physical effort, and cold. The frequency of the spells, for Mr R. D. is once every other month; each spell lasts 8 days, on the average. Treatments with the combination of the alkaloids of ergot and with vincamine are entirely unsuccessful. Thus, M. R. D.'s professional and family life are particularly perturbed. The patient is then administered daily 5 tablets containing each 150 mg derivative No. 1, during 7 weeks.

As soon as this treatment is started, the spells cease and the pains are relieved within the first 24 hours. M. R.D. is then able to resume a more sustained activity in his hospital service. From a biological standpoint, the results summarized below reflect a marked improvement.

| Control tests | Before treatment | After treatment |
| --- | --- | --- |
| Red blood corpuscules | 3,500,000 | 3,600,000 |
| White blood corpuscules | 7,000 | 7,500 |
| Hemoglobin | 10 g | 10 g |
| Hematocrite | 36% | 37% |
| Total Bilirubin | 40 | 17 |
| Reticulocytes | 11% | 10% |

Case Report No. 4

Mrs. B. D., 22 years old, is an African housewife. She suffers from drepanocytic anemia which was diagnosed by electrophoresis. She was hospitalized a number of times because of very frequently repetitive drepanocytic spells. She is unable to take care of her housework, because she suffers from extreme asthenia and listlessness. The slightest physical effort, just as cold baths and sharp dropping of the temperature induce important drepanocytic spells. Vincamine or the combination of the alkaloids from ergot were found inactive in her case. She was then prescribed a daily dosage regimen of 3 coated tablets containing each 200 mg of derivative No. 4. She was under said treatment for a period of time of 8 weeks; as early as the very first days, however, the drepanocytic spells disappeared and the asthenia was substantially reduced and Mrs. B. S. was then able to resume sufficient activity to take care of her housework. The biological results obtained confirm said improvement.

| Control tests | Before treatment | After treatment |
| --- | --- | --- |
| Red blood corpuscules | 2,500,000 | 2,800,000 |
| White blood corpuscules | 10,000 | 2,500 |
| Hemoglobin | 7 g | 7.5 g |
| Hematocrite | 24% | 25% |
| Total Bilirubin | 35 | 35 |
| Reticulocytes | 10% | 10% |

Case Report No. 5

Young S. L., 7 years old, suffers from drepanocytic anemia which was diagnosed by electrophoresis at the age of 2½ years. He was hospitalized for diffuse pains and has drepanocytic spells whenever he indulges in physical effort or takes a cold bath. Such spells occur regularly, 2–4 times a month on the average; they generally last 3 days. While treatment with the combination of the alkaloids of ergot brought about a slight relief, treatment with vincamine was found to be inactive. The patient is administered for a period of time of 2 months a daily dosage regimen of 2 capsules containing each 200 mg of derivative No. 3. The spells disappear completely and rapidly, and clinical improvement is satisfactory. This young African boy is then able to go home, to attend school again and to play games with his classmates. Said clinical improvement is confirmed by the following biological improvement:

| Control tests | Before treatment | After treatment |
| --- | --- | --- |
| Red blood corpuscules | 3,000,000 | 3,000,000 |
| White blood corpuscules | 6,500 | 6,800 |
| Hemoglobin | 9 g | 9.5 g |
| Hematocrite | 30% | 30% |
| Total Bilirubin | 30 | 25 |
| Reticulocytes | 10% | 10% |

It is thus apparent, from the above data, that the derivatives of the formula (I) are particularly valuable, both for preventive and for curative purposes, for the treatment of drepanocytosis.

For oral administration, they may be formulated as tablets, coated tablets, capsules, drops and syrups.

Each unit dose contains advantageously 100–500 mg active ingredient. The daily dosage regimen may vary within the range of from 500 mg to 1000 mg active ingredient, depending on the severity of the drepanocytic condition.

Having now described our invention what we claim as new and desire to secure by Letters Patent is:

1. A method for the treatment of a patient suffering from drepanocytic anemia and showing the symptoms of drepanocytosis caused by the presence of S-hemoglobin in drepanocytes, which comprises:
  administering to said patient a compound of formula I below, thus inducing reversal of the drepanocytosis by causing the drepanocytes to lose their sickle shape and revert to their disk-like shape,
  increasing the hemoglobin content and causing a remission of the symptoms of said patient;

said compound being administered in a daily dosage of from about 400 to about 1000 mg. as the active medicament, and having the formula:

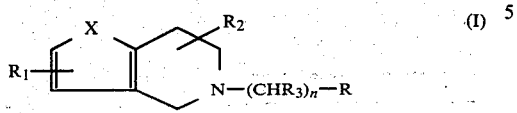 (I)

in which X is oxygen or sulfur; R is selected from the group consisting of hydrogen, phenyl, phenyl substituted with at least one group selected from the group consisting of halogen, lower alkyl, lower alkoxy, nitro, amino, sulfonylamino, aryl, carboxyl, alkoxycarbonyl, cyano, hydroxymethyl and methylenedioxy; stryryl, naphthyl, thienyl, benzhydryl, each of the latter being optionally substituted with at least one group selected from the group consisting of halogen, lower alkyl, lower alkoxy, aryl, nitro, amino, sulfonylamino, carboxyl, alkoxycarbonyl, cyano, hydroxymethyl and methylenedioxy; benzoyl, and benzoyl substituted with at least one group selected from the group consisting of halogen, lower alkyl, lower alkoxy, nitro, amino and sulfonylamino; $R_1$ and $R_2$ each represent at least one atom or group selected from the group consisting of hydrogen, halogen, hydroxy, lower alkyl, lower alkoxy, nitro and amino; $R_3$ is selected from the group consisting of hydrogen, halogen, hydroxy, lower alkyl, lower alkoxy, nitro and amino; and n is zero or an integer from 1 to 15; and $R_3$ may have a different meaning in each $CHR_3$ group when n is greater than 1; or a pharmaceutically acceptable acid addition salt or quaternary ammonium derivative of said compound.

2. The method of claim 1 wherein the daily dosage is administered in unit dosages of from about 100 to about 500 mg.

3. The method of claim 2 wherein the medicament is administered orally in dosage units of about 150 to about 250 mg.

4. The method of claim 1 wherein the compound is selected from the group consisting of:
5-(2-chloro-benzyl)-4,5,6,7-tetrahydrothieno pyridine hydrochloride;
5-(2-hydroxy-2-phenyl-ethyl)-4,5,6,7-tetrahydrothieno pyridine hydrochloride; 5-o-carboxybenzyl-4,5,6,7-tetrahydrothieno pyridine and 5-p-chlorobenzyl-4,5,6,7-tetrahydrothieno pyridine hydrochloride.

5. A method for the treatment of a patient having the genetic defect which induces drepanocytic anemia which comprises administering to such a patient an effective amount of a compound having the formula:

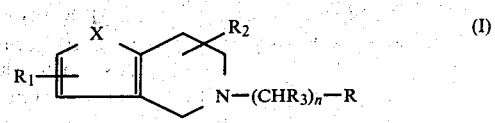 (I)

in which X is oxygen or sulfur; R is selected from the group consisting of hydrogen, phenyl, phenyl substituted with at least one group selected from the group consisting of halogen, lower alkyl, lower alkoxy, nitro, amino, sulfonylamino, aryl, carboxyl, alkoxycarbonyl, cyano, hydroxymethyl and methylenedioxy; stryryl, naphthyl, thienyl, benzhydryl, each of the latter being optionally substituted with at least one group selected from the group consisting of halogen, lower alkyl, lower alkoxy, aryl, nitro, amino, sulfonylamino, carboxyl, alkoxycarbonyl, cyano, hydroxymethyl and methylenedioxy; benzoyl, and benzoyl substituted with at least one group selected from the group consisting of halogen, lower alkyl, lower alkoxy, nitro, amino and sulfonylamino; $R_1$ and $R_2$ each represent at least one atom or group selected from the group consisting of hydrogen, halogen, hydroxy, lower alkyl, lower alkoxy, nitro and amino; $R_3$ is selected from the group consisting of hydrogen, halogen, hydroxy, lower alkyl, lower alkoxy, nitro and amino; and n is zero or an integer from 1 to 15; and $R_3$ may have a different meaning in each $CHR_3$ group when n is greater than 1; or a pharmaceutically acceptable acid and inhibiting intravascular falciformation of red blood corpuscles which cause drepanocytic anemia.

6. The method of claim 5 wherein the daily dosage is administered in unit dosages of from about 100 to about 500 mg. of active ingredient.

7. The method of claim 6 wherein the medicament is administered orally in dosage units of about 150 to about 250 mg.

8. The method of claim 5 wherein the compound is selected from the group consisting of:
5-(2-chloro-benzyl)-4,5,6,7-tetrahydrothieno pyridine hydrochloride;
5-(2-hydroxy-2-phenyl-ethyl)-4,5,6,7-tetrahydrothieno pyridine hydrochloride; 5-o-carboxybenzyl-4,5,6,7-tetrahydrothieno pyridine and 5-p-chlorobenzyl-4,5,6,7-tetrahydrothieno pyridine hydrochloride.

9. The method of claim 8 wherein the compound is 5-(2-chloro-benzyl)-4,5,6,7-tetrahydrothieno pyridine hydrochloride.

10. The method of claim 4 wherein the compound is 5-(2-chloro-benzyl)-4,5,6,7-tetrahydrothieno pyridine hydrochloride.

* * * * *